United States Patent [19]

Schoenig, Jr. et al.

[11] Patent Number: 4,857,260
[45] Date of Patent: Aug. 15, 1989

[54] APPARATUS FOR ASSEMBLING AND WELDING END PLUGS TO NUCLEAR FUEL CLADDING TUBES AND INSPECTING THE END PLUG WELDS ON AN AUTOMATED BASIS

[75] Inventors: Frederick C. Schoenig, Jr.; Edward S. Walker, both of Wilmington, N.C.; Michael K. Cueman, Niskayuna, N.Y.; Robert A. Haughton; Jaime A. Zuloaga, Jr., both of Wilmington, N.C.

[73] Assignee: General Electric Company, San Jose, Calif.

[21] Appl. No.: 250,059

[22] Filed: Sep. 28, 1988

[51] Int. Cl.⁴ .................. G21C 21/00; G21C 17/00
[52] U.S. Cl. .................................. 376/245; 376/261; 29/723
[58] Field of Search ............... 376/261, 260, 252, 251, 376/248, 245, 451, 450; 29/723, 705, 791, DIG. 13; 219/136; 228/60; 73/618; 53/477, 284, 285

[56] References Cited

U.S. PATENT DOCUMENTS 4,554,128 11/1985 Parker et al. ................... 376/245
4,687,605 8/1987 Cellier et al. ................... 376/261

Primary Examiner—Brooks H. Hunt
Assistant Examiner—Daniel Wasil
Attorney, Agent, or Firm—Robert R. Schroeder

[57] ABSTRACT

In an automated first weld apparatus, a transporter conveys nuclear fuel cladding tubes successively to a welding station where a separate end plug is welded to an open end of each tube. Thereafter, the transporter indexes the tubes successsively through a cooldown station where the weld is cooled, to a reader station where a unique end plug serial number is read, and then to a succession of inspection stations where the internal and external weld characteristics are automatically examined. The resulting inspection data is correlated with the associated serial number for record purposes and tested against quality assurance standards pursuant to sorting the tubes into accepted and rejected lots.

35 Claims, 16 Drawing Sheets

APPARATUS FOR ASSEMBLING AND WELDING END PLUGS TO NUCLEAR FUEL CLADDING TUBES AND INSPECTING THE END PLUG WELDS ON AN AUTOMATED BASIS

The present invention relates to automated apparatus for expediting handling, processing, and quality inspection procedures involved in the manufacture of nuclear fuel rods.

BACKGROUND OF THE INVENTION

A nuclear fuel rod is comprised of a column of fuel pellets sealed in an elongated cladding tube typically formed of a zirconium alloy. In the process of manufacturing nuclear fuel rods, the first major operation prior to loading the tubes with fuel pellets is to seal off one of their open ends by welding an end plug thereto in a first weld operation. In accordance with established practice, tubes are brought to a welding table where an operator utilizes equipment to mate an end plug with an open end of each of a succession of tubes. The mated items are then welded together using an inert gas-arc welder and, after the weld has cooled sufficiently, a quality assurance technician inspects the weld to determine if it meets predetermined quality control standards, including, inter alia, weld integrity and weld bead diameter. Following inspection, the welded tube is placed in the appropriate accept or reject trays, and the welding operation begins anew on the next tube. After a pre-established number of acceptable tubes have accumulated, all or a selected number thereof may be subjected to additional quality assurance tests and then transported to a fuel loading operation.

It is thus seen that this welding operation is a time consuming, labor intensive process. Human participation in the welding and quality assurance operations with respect to each first end plug weld imposes a serious bottleneck on nuclear fuel rod production. This problem is exacerbated because each end plug weld must cool in the inert gas environment of the welder to avoid undesirable oxidation of the weld. Thus, otherwise productive time is spent waiting for a weld to cool rather than welding another end plug to another tube. Furthermore, because some quality assurance inspections are made on individual tubes while at the weld table, additional delays enter the process, further reducing productivity. Moreover, if the first end plug weld is created as a flush weld, rather than a bead weld, visual inspection is an inadequate test of weld integrity.

Human participation in the welding and inspection operations also can have a detrimental effect on the fuel rod quality. As the amount of handling increases, so does the possibility of scratching the tube surfaces. Exterior surface scratches negatively impact fuel rod integrity and lifetime due to an increased likelihood of corrosion thereat; furthermore, they lack cosmetic appeal, which is important to some customers.

OBJECTS OF THE INVENTION

It is an object of the present invention to provide new and improved apparatus for welding an end plug to an open end of a nuclear fuel cladding tube.

Another object of the present invention is to provide automated apparatus for welding a separate end plug to a plurality of tubes in rapid succession.

Yet another object of the present invention is to provide automated apparatus of the above-character, wherein the end plug welds and the tubes are inspected for quality assurance.

A further object of the present invention is to provide automated apparatus of the above-character, wherein quality assurance inspection is performed on each and every end plug weld without human intervention.

A still further object of the present invention is to provide automated apparatus of the above-character, wherein productivity is dramatically increased, while labor content is minimized.

It is yet a further object of the present invention to provide automated apparatus of the above-character, wherein the operations of end plug welding and the various quality assurance inspections are performed in tandem with respect to a plurality of tubes at an expeditious rate.

Still another object of the present invention is to provide automated apparatus of the above-character, wherein quality assurance inspection data are collected and collated with respect to each end plug-welded tube.

Yet another object of the present invention is to provide automated apparatus of the above-character, wherein the individual tubes are transported successively through the various operating stations of the apparatus in a reliable and safe manner.

Other objects of the invention will in part be obvious and in part appear hereinafter.

SUMMARY OF THE INVENTION

The foregoing objects of the present invention are achieved by providing automated first weld apparatus for welding end plugs to nuclear fuel cladding tubes and thereafter conducting a series of inspections of each end plug weld to determine whether it meets established quality assurance standards, all in rapid succession. The apparatus includes an input queue for accumulating a plurality of tubes; a welding station where an end plug is welded to an open end of each tube; a cooldown station for rapidly cooling the end plug weld; a reader station for reading the serial number imprinted on each end plug; an inspection station where each end plug weld is ultrasonically inspected for integrity; and a tube transporter for conveying each tube to each of these stations in succession.

The apparatus preferably also includes a second weld inspection station where weld diameter and end plug-tube concentricity are guaged for acceptability, and a barrier inspection station where the presence and thickness of any zirconium interior tube liner are determined. The data obtained from these various inspection stations are gathered by data acquisition means, collated on the basis of end plug serial numbers, and compared against predetermined quality control standards to determine whether the end plug welds are acceptable or rejectable. As a result of this determination, the tubes are automatically sorted into accepted and rejected lots. The automated first weld apparatus of the present invention preferably further includes a rod accumulator to which accepted tubes are conveyed for visual inspection by a quality assurance technician.

These and other objects of the present invention, along with features and advantages thereof, will become apparent from the following detailed specification when read in conjunction with the accompanying drawings.

BRIEF DESCRIPTION OF THE DRAWINGS

Corresponding reference numerals refer to like parts throughout the several views of the drawings.

DETAILED DESCRIPTION OF THE INVENTION

Figure 1:
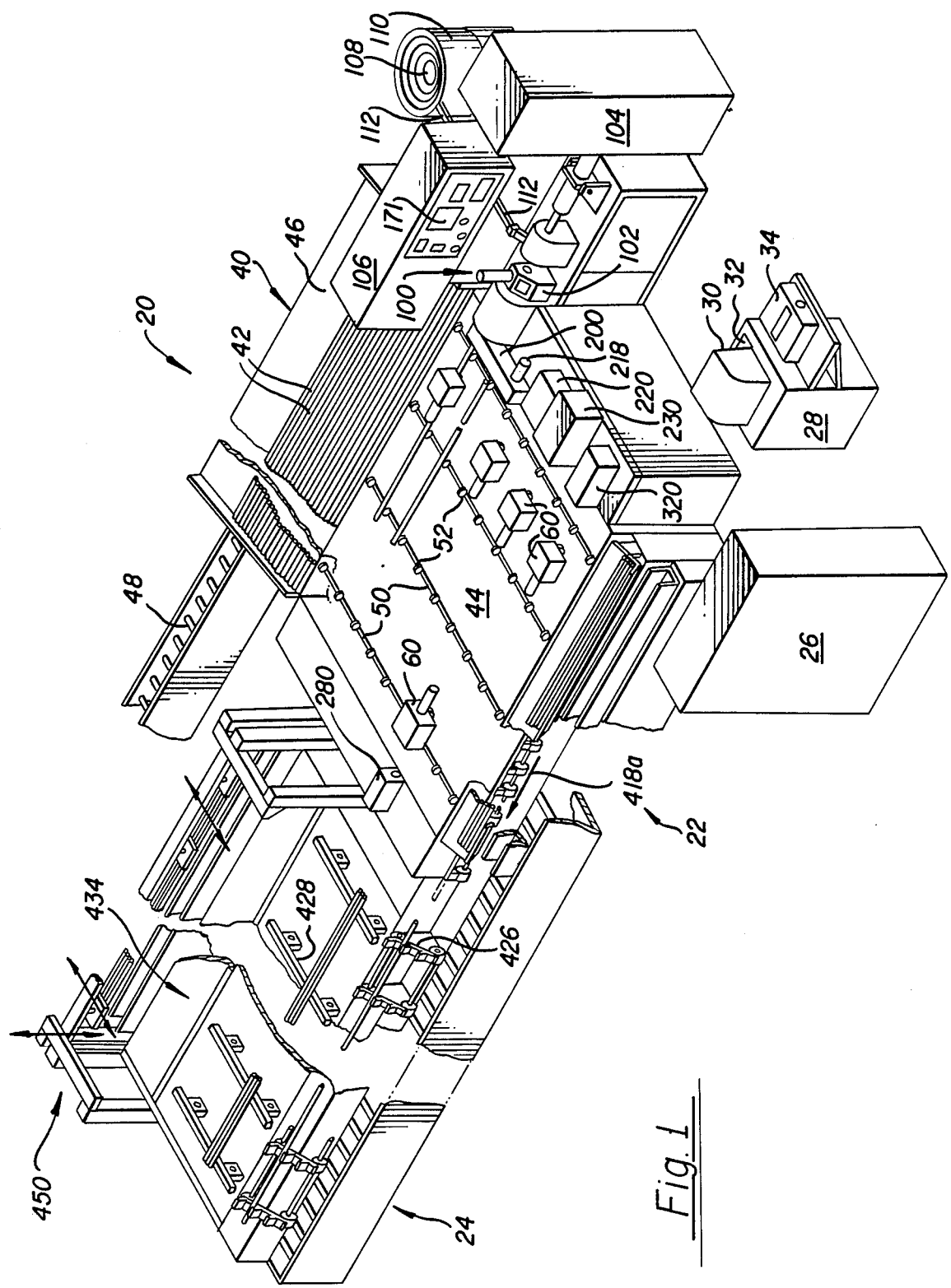
FIG. 1 depicts in perspective an exemplary embodiment in accordance with the present invention of an automated first weld apparatus for welding an end plug to an open end of a succession of nuclear fuel rod cladding tubes and for performing quality assurance inspection of the end plug welds and tubes.

The first weld apparatus of the present invention, generally indicated at 20 in FIG. 1, comprises two major sections: an automated welding and inspection section generally indicated at 22 and an automated offload accumulator and visual inspection section, generally indicated at 24. Control of apparatus 20 is generally effected by a process controller 26, such as a General Electric Series Six Programmable Logic Controller (PLC). This process controller is linked with a computer system 28, which may include a data acquisition computer, such as a PDP 11/73, and a data analysis computer, such as a VAX Station 11/GPX, both manufactured by Digital Equipment Corporation. The computer system is housed in a console which includes, inter alia, a CRT monitor 30, a keyboard 32 for selecting operating and display modes, and a printer 34 for providing a hard copy record of operating parameters and inspection test results.

Still referring to FIG. 1, welding and inspection section 22 includes an input queue 40 capable of holding a supply of cladding tubes 42 and a tube transporter 44 for indexing individual tubes from the input queue to a succession of operating stations to be described. Input queue 40 comprises an inclined feed table 46 on which a supply of tubes 42 is supported. The tubes roll down on the feed table to its lower edge where they are picked up one-by-one by tube transporter 44. To assure reliable feeding of the tubes onto the transporter, suitable means (not shown) are provided to progressively increase the inclination of the feed table as the supply of tubes in the input queue diminishes. Input queue 40 further includes a roller conveyor 48 on which trays (not shown) of cladding tubes are conveyed and from which tubes are manually loaded onto feed table 46 prior to initiation of the automated welding and inspection operations.

Tube transporter 44 periodically picks up each tube 42 as presented at the feed table lower edge and transports it successively from station to station. This transporter comprises a plurality of parallel, spaced conveyor chains 50 which are commonly driven in synchronous, indexing movement. Each conveyor chain carries a plurality of correspondingly spaced, grooved rollers 52 such as to provide a succession of straight line tube supports transverse to the direction of their indexing movement. To minimize scratching of the tube surface, these rollers are preferably formed of plastic. The spacing between adjacent rollers 52 on each conveyor chain 50 is equal to the separation between the various operating stations to which each tube is successively presented. Thus, each time the conveyor chains 50 index one position under the control of process controller 26, each tube supported in the roller grooves is moved a distance equal to the spacing between adjacent rollers and therefore from one station to the next. Each roller 52 is free to rotate about its axis, which is aligned parallel to the direction of tube transport, thereby facilitating endwise or axial movement of the tubes into and out of the various operating stations. The number of conveyor chains utilized depends in part upon the degree of intermittent support needed to maintain the tubes in a substantially straight configuration with minimal sagging between rollers. Sensors (not shown) stationed at each index position signal process controller 26 that the tubes are properly supported by the transporter and are in position to be reciprocated into and out of the various operating stations.

Figure 2:
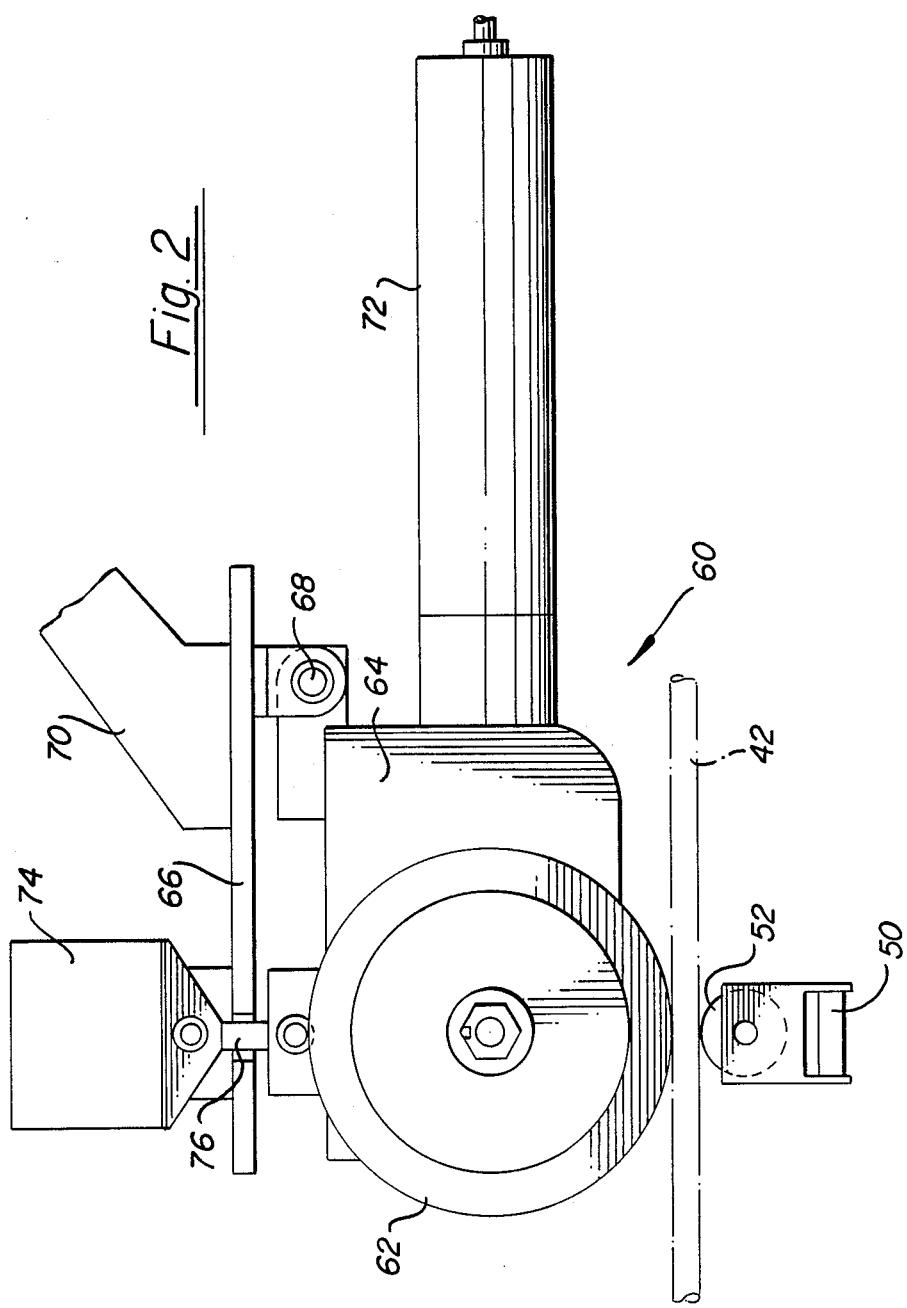
FIG. 2 illustrates one of several pinch wheel drive mechanisms for axially reciprocating a cladding tube into and out of the various operating stations of the first weld apparatus of FIG. 1.

Rod transporter 44 further includes a plurality of pinch wheel drives 60 to reciprocate the cladding tubes axially into and out of the various stations, as seen in FIG. 1. These pinch wheel drives 60, as detailed in FIG. 2, are suspended above tube transporter 44 at the various index positions aligned with those operating stations into which tubes are to be reciprocated to drop a pinch wheel 62 into driving engagement with the tube thereat. The pinch wheel is rotatably mounted by a frame 64 which is pivotally mounted to a support plate 66, as indicated at 68. This support plate is affixed to a rigid arm 70 suspending the pinch wheel drive in position. Frame 64 also carries a motor 72 which propels pinch wheel 62 via a suitable right angle gear drive (not shown). An air cylinder 74 is supported by plate 66 with its piston 76 connected with frame 64.

It is thus seen that actuation of this air cylinder under the control of process controller 26 extends its piston 76 to drop pinch wheel 62 into engagement with a tube 42 at a location immediately above a tube supporting transporter roller 52. Energization of motor 72 by the process controller drives pinch wheel to propel the tube into an operating station. Once properly positioned therein, motor 72 is de-energized, and piston 76 is retracted, either pneumatically or by a return spring (not shown) to lift the pinch wheel from engagement with the tube. After completion of the operation at the particular station, air cylinder 74 is again actuated to drop the pinch wheel back into engagement with the tube, and motor 72 is energized in reverse to propel the tube back out of the station. When the tube is out on transporter 44, the motor is de-energized, and the pinch wheel is elevated out of contact with the tube. Suitable sensors (not shown) linked to process controller 26 (FIG. 1) monitor tube movement and position and pinch wheel drive operation pursuant to controlling the operation thereof.

Welding and inspection section 22 further includes a plurality of stations where welding and inspection operations occur. The first one of these stations to which each tube 42 is presented is a welding station, shown generally at 100 in FIG. 1. This welding station includes as suitable welder 102, such as a TIG welder, with its associated power supply 104 and control panel 106. Located at the welding station is a supply of end plugs 108, contained in a vibratory bowl feeder 110, from which end plugs are successively delivered along a track 112. The individual end plugs are extracted from the track exit by a pick and place mechanism and mated to the open end of a tube 42 presented at welding station 100.

Figure 3:
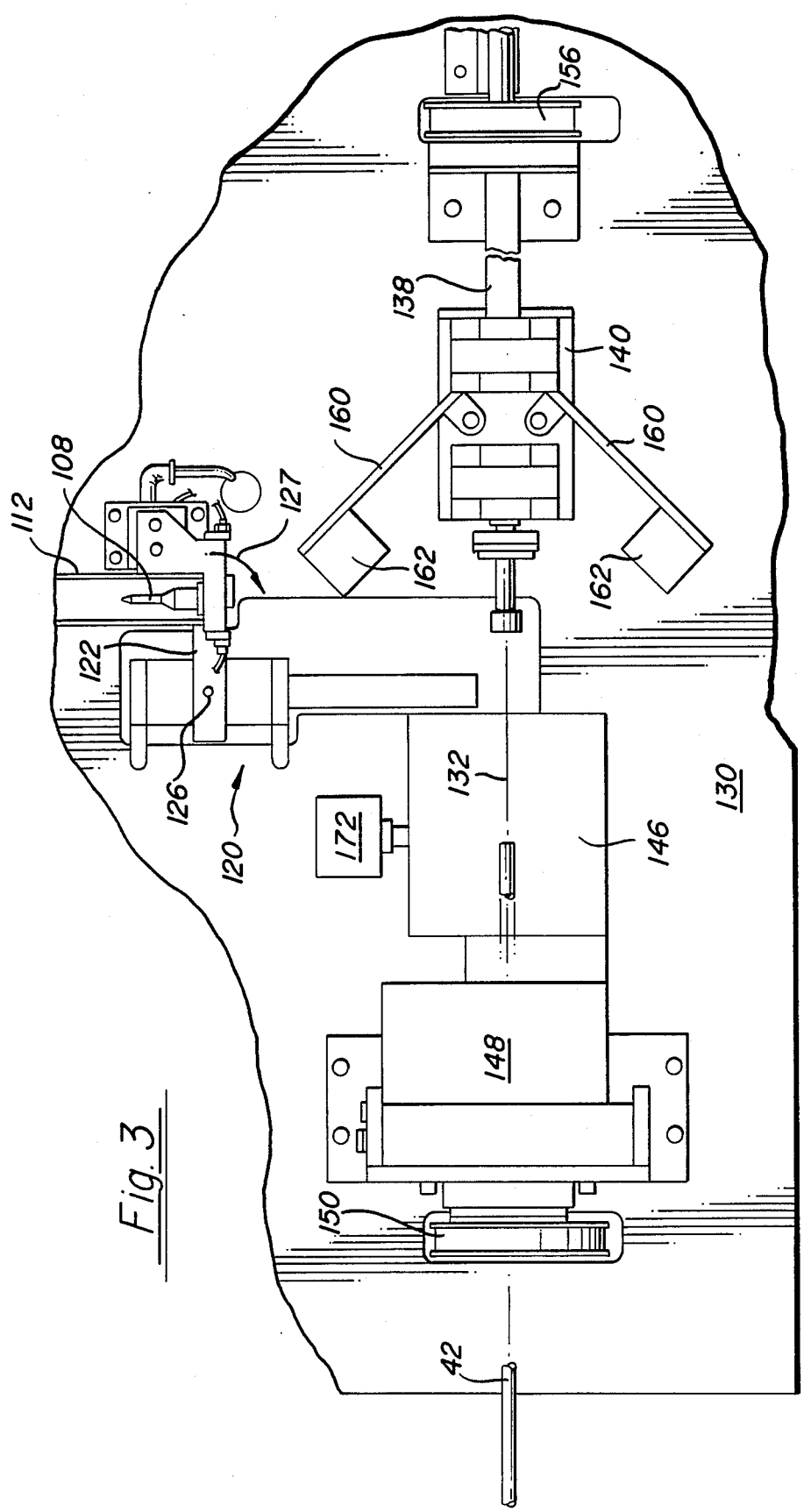
FIG. 3 is a plan view of the end plug welding station included in the first weld apparatus of FIG. 1.
Figure 5:
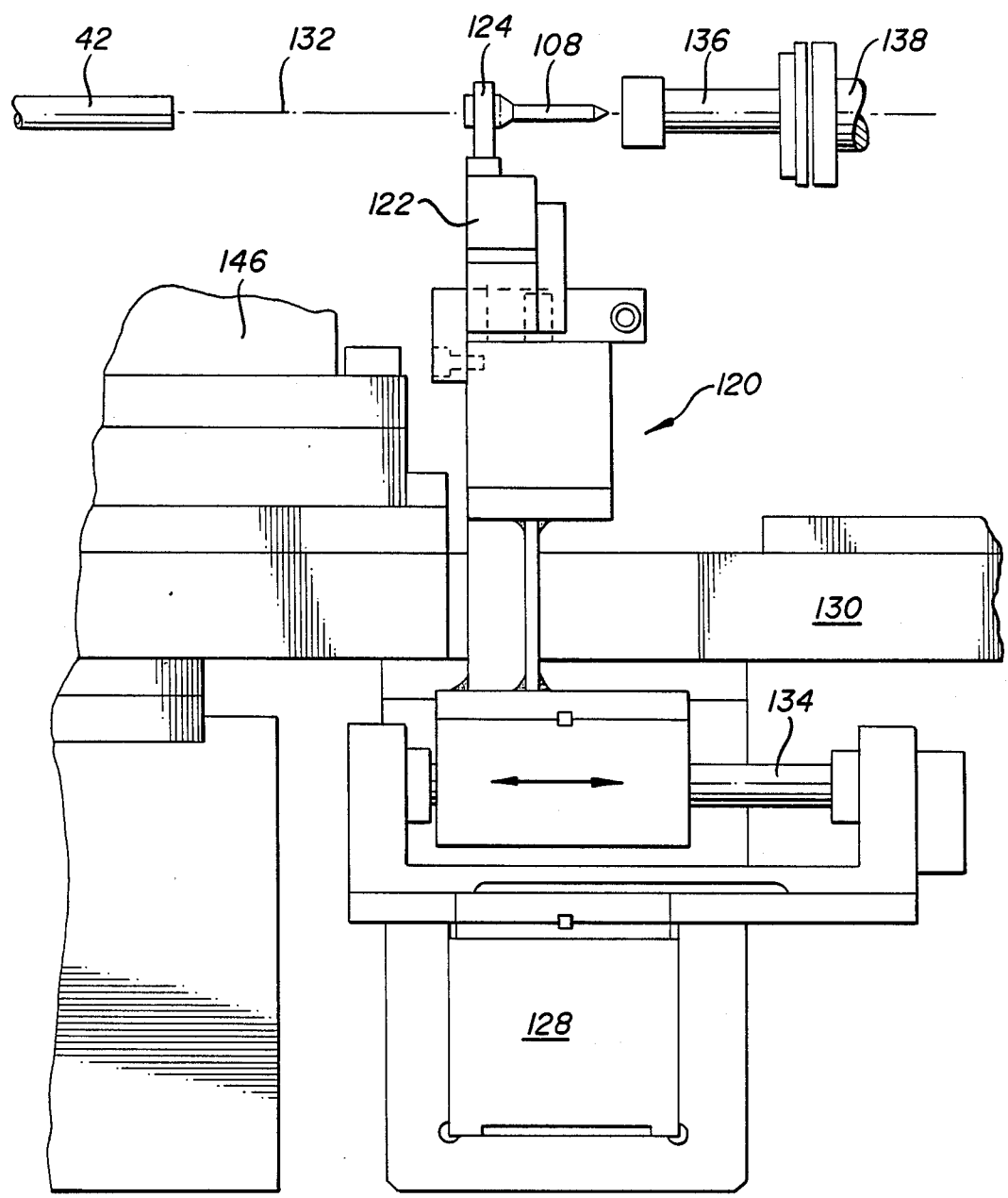
FIG. 5 is an enlarged, fragmentary elevational view of the welding station illustrating the end plug pick and place mechanism.

The pick and place mechanism, generally indicated at 120 in FIGS. 3 and 5, includes an arm 122 mounting at its free end gripper fingers 124 which are articulated to grasp the base end of each end plug as it is presented at the exit of bowl feeder track 112. Arm 122 is pivotally mounted at 126 (FIG. 3) to swing through a 90° arc in the illustrated clockwise direction as indicated by arrow 127, thus rotating the axis of the grasped end plug 90°. The pick and place mechanism is then translated horizontally (downwardly in FIG. 3) on a transverse slide 128 mounted beneath weld station table 130 (FIG. 5). This motion brings the grasped end plug 108 into a position with its axis aligned with the axis, indicated at 132, of a tube 42 conveyed into the weld station. Once this axial alignment is achieved, the pick and place mechanism 120 is translated axially on a longitudinal slide 134 carried by the transverse slide to insert the pointed end of the plug into an adaptor 136. The pick and place mechanism then releases the end plug and retraces its movements back to the feed bowl track exit to pick up another end plug. Again, operation of the pick and place mechanism is controlled by controller 26.

Figure 4:
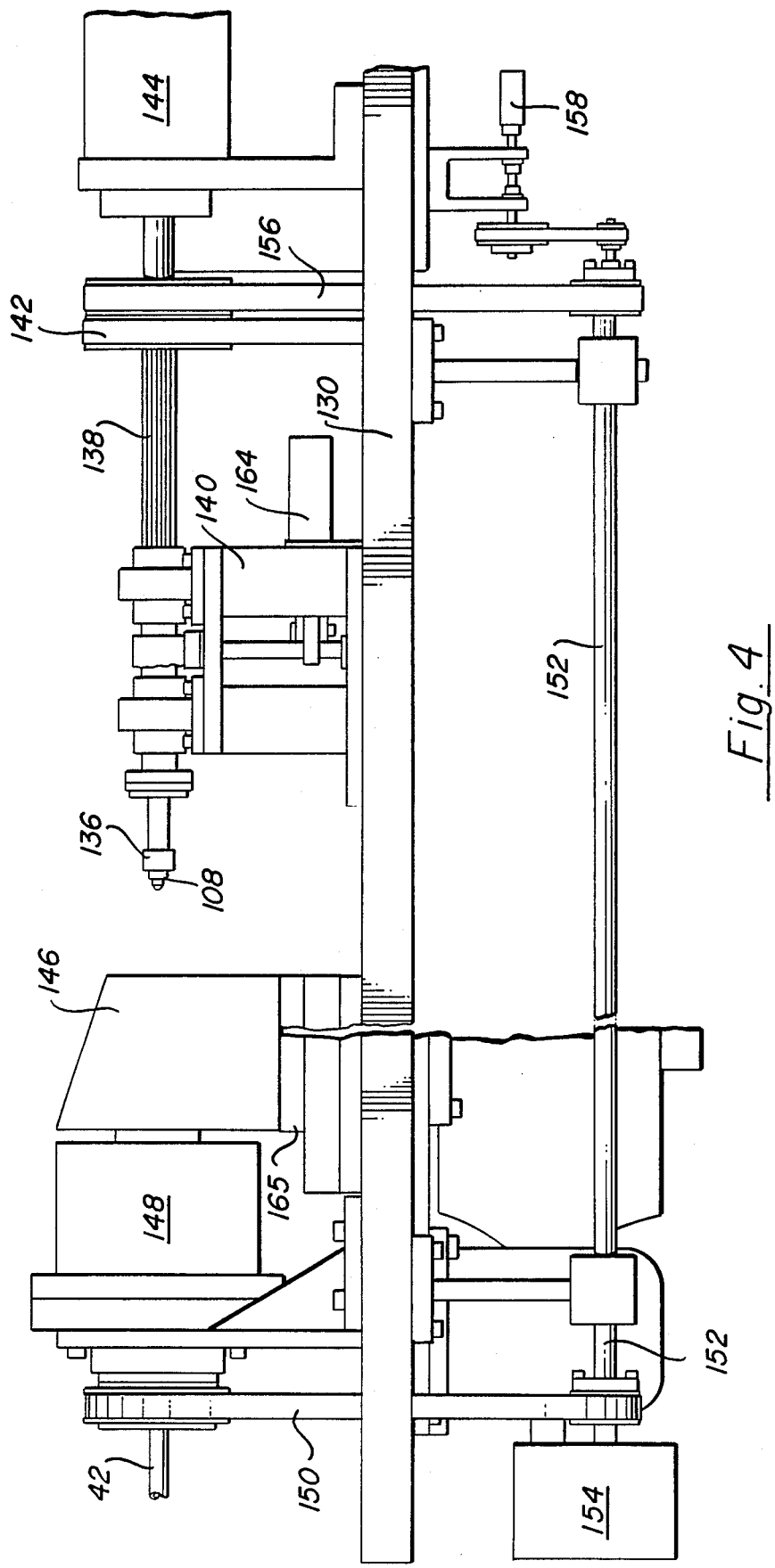
FIG. 4 is a side elevational view of the welding station.

Referring now to FIG. 4, adapter 136 is carried at the end of a splined shaft 138 mounted in an elevated position above weld table 130 by a stanchion 140 and a journal 142 for both rotary and reciprocating motion. Shaft 138 is reciprocated by an air cylinder 144 to drive an end plug 108 held by adapter 136 into a weld box 146 in ram fashion where it is inserted into the open end of a tube 42 propelled into weld station 100 by the associated pinch wheel drive 60 (FIG. 1). The tube is clamped by an air chuck 148 and rotated by a belt drive 150 taken off a jack shaft 152 driven by a motor 154. Spline shaft 138 is rotated in synchronism with the air chuck by a belt drive 156 taken off of jack shaft 152, and thus the tube and end plug are rotating at the same speed as they are mated and welded together within weld box 146. A tachometer 158 is also driven off jack shaft 152 to provide a reading of tube angular velocity to welder display panel 106 and controller 26, which is a controlled welding operating parameter.

As seen in FIG. 3, stanchion 140 mounts a pair of pivotal arms 160, each carrying at its free end a heating element 162. These arms are actuated by an air cylinder 164 (FIG. 4) to swing toward each other, bringing the heating elements into embracing relation with adapter 136. This procedure is initiated at the beginning of an end plug welding run to preheat the adapter and thus avoid any prejudicial heat sinking effect on the weld quality posed by a cold adapter. Generally, adapter preheating is required only prior to the initial end plug weld. Thereafter, the requisite adapter temperature is maintained by the successive welding operations. Thus the heating elements are held in their retracted position seen in FIG. 3 during a production run.

Figure 6:
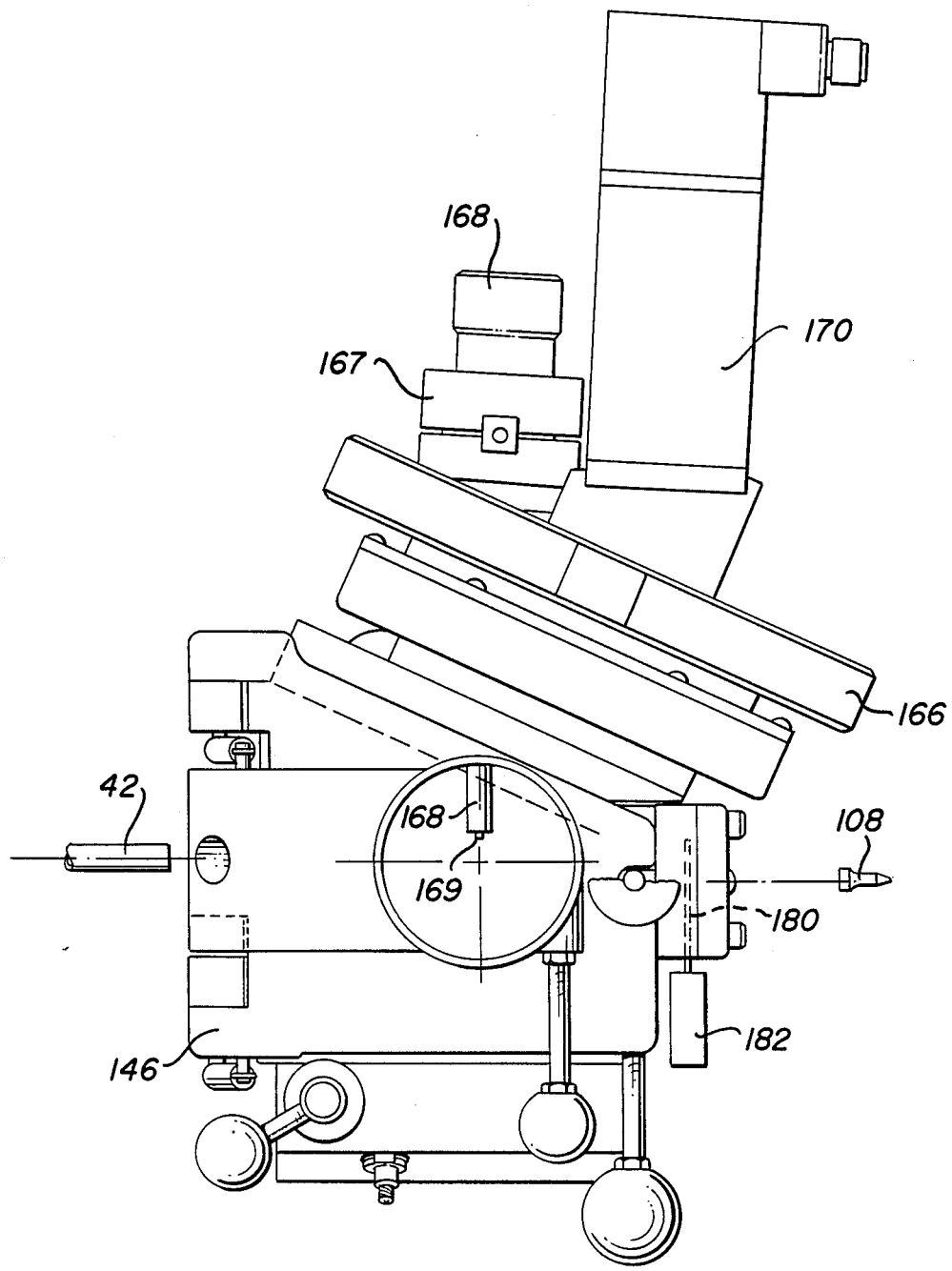
FIG. 6 is a side view of the weld box included in the welding station.
Figure 7:
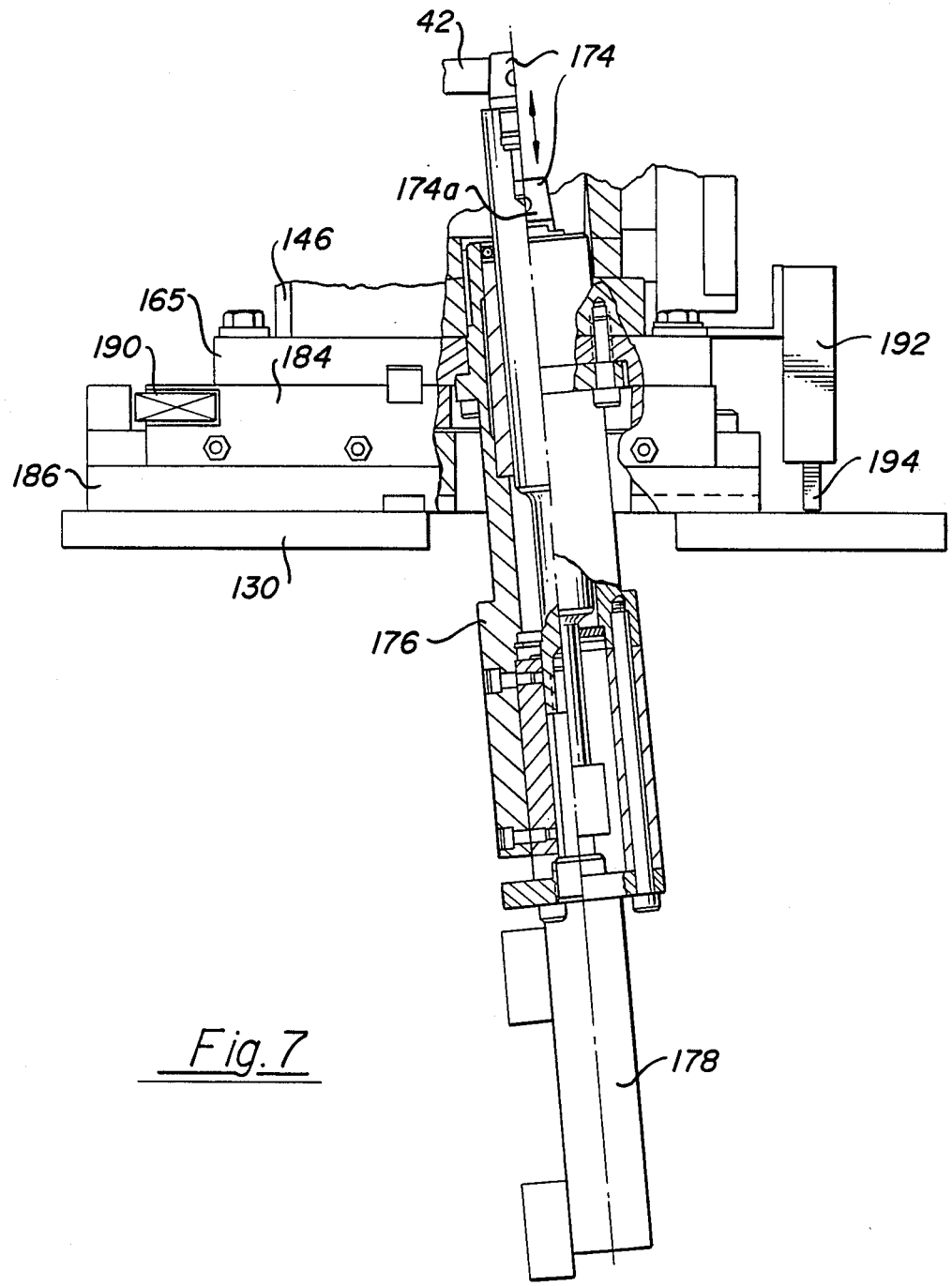
FIG. 7 is fragmentary side elevational view, partially broken away, of the weld box.

Referring jointly to FIGS. 4, 6 and 7, weld box 146 is mounted on a base 165 and carries a turret 166 mounting a holder 167 for a welding torch 168 and electrode 169 and a torch positioning motor 170. The turret is rotated to angularly position the torch relative to the mated end plug 108 and tube 42 for either a flush weld or a bead weld. Motor 170 is selectively energized to adjust the torch and electrode to an appropriate weld-start position prior to a first weld production run. This adjustment is facilitated by observing a TV monitor 171 included in welder control panel 106 (FIG. 1) where an image of the torch-electrode position is generated by a TV camera 172 (FIG. 3) mounted to weld box 146.

As a tube 42 is driven into the weld box by the associated pinch wheel drive 60, its leading end encounters a retractable stop 174 carried by a holder 176 affixed to weld box base 165, as seen in FIG. 7. The pinch wheel drive stalls and is stopped as air chuck 148 (FIG. 5) clamps the tube. Stop 174 is retracted downwardly to its position 174a seen in FIG. 7 by an air cylinder 178, and motor 154 is energized to drive the air chuck and thus rotate tube 42. Air cylinder 144 is then actuated to ram the synchronously rotating end plug 108 held by adapter 136 into mating engagement with the open end of the tube (FIG. 4). Admittance of the end plug into weld box 146 is permitted by the retraction of a shutter 180 upon actuation of an air cylinder 182. The weld power supply program entered into control panel 106 (FIG. 1) establishes the requisite helium gas flow into the weld box and the tube-end plug rotational speed, and then sequences the welding operation through arc start, weld profile and post weld gas flow time. To establish a proper alignment of the welding torch electrode 169 with the tube-end plug seam prior to the welding operation, weld box base 165 is affixed to a slide 184 carried by a slide base 186 secured to table 130 (FIG. 7) supporting the various welding station components. As the ram air cylinder 144 seats an end plug in a tube open end, weld box 146 is incrementally shifted leftward to compress a compression spring 190 acting between slide 184 and slide base 186. A brake in the form of an air cylinder 192 mounted to weld box base 165 is actuated to extend piston 194 into braking engagement with the surface of table 130. The position of the weld box is held by this brake as the ram air cylinder pressure is reduced to avoid weld mushrooming during the welding operation. Upon completion of an end plug weld, motor 154 is de-energized, and the synchronous rotations of air chuck 148 and adapter 136 come to a halt. The air chuck releases the tube, and the adapter is retracted by ram air cylinder 144. The associated pinch wheel drive is then activated to withdraw the tube from weld station 100.

While not shown, preferably means are provided to lift a tube from its transporter supported rollers once it is axially positioned within the weld box 146 by stop 174. Arms are then deployed to positively control the radial position of the tube as it is being rotated by air chuck 148. At the conclusion of an end plug weld, the tube is returned to its position on the transporter rollers 52 for withdrawal from the weld station by the associated pinch wheel drive 60.

As shown in FIG. 1, following completion of the end plug welding operation, the tube is retracted from welding station 100 by its associated pinch wheel drive 60 and is conveyed in several indexing steps through a cooldown station 200 by tube transporter 40. While in the cooldown station, the end plug weld is cooled in a non-oxidizing atmosphere to a temperature below that at which the weld and contiguous tube and end plug material readily oxidizes. Since most cladding tubes and end plugs are made of zircalloy, cooling the welded end portion of the tube to a temperature below 40° C. should suffice to prevent discolorating oxidation of the welded parts.

Figure 8:
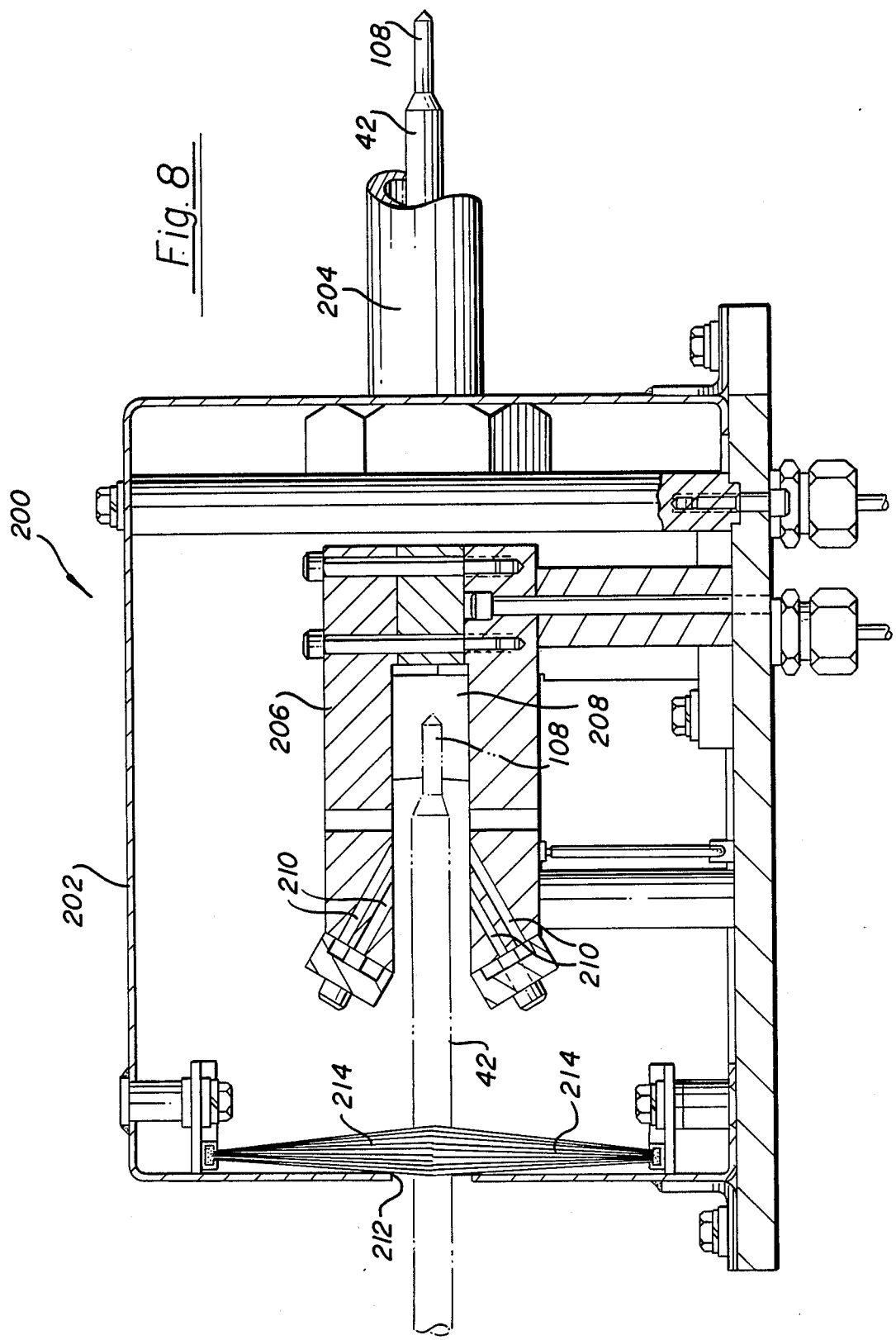
FIG. 8 depicts in cross section a cooldown station utilized in the first weld apparatus of FIG. 1 to rapidly cool an end plug weld.

Cooldown station 200, depicted in cross section in FIG. 8, comprises a substantially box-shaped enclosure 202 of a length dependent upon the number of transporter indexed cooling positions to be accommodated requisite to achieving the desired cooldown temperature. Reciprocation of a tube 42 into and out of the weld station is effected through the cooldown station enclosure and a transition tube 204 whose entry end is open to the interior of enclosure. Mounted within this enclosure is a horizontally elongated manifold 206 defining a channel 208 through which the end plug weld end of the tube is translated in plural indexing steps by transporter 44. The manifold is provided with a distributed array of jets 210 arranged to direct blasts of non-oxidizing, cooling gas, such as argon, against the end plug weld. This enclosure is completely closed except for a frontal opening 212 extending substantially the length of cooldown enclosure 202. This window is substantially obstructed to prevent the entry of the ambient air into enclosure 202 by a curtain 214. As shown in FIG. 8, this curtain comprises a pair of opposed bristle brushes mounted within the enclosure with their free ends blending together at the plane of horizontal, indexing movement of the tubes. This brush curtain provides an effective barrier to the penetration of ambient air, thus preserving the non-oxidizing, inert gas atmosphere within housing 202 as the tubes are indexed therethrough. When a tube reaches the last index position within the cooldown station enclosure, it is backed out fully onto transporter 44 just prior to the next index step by a pinch wheel drive or by a separate translator, such as an air cylinder illustrated at 218 in FIG. 1.

Returning to FIG. 1, automated first weld apparatus 20 further includes a serial number reader station 220 to which the successive tubes are next indexed by transporter 44. Each end plug has imprinted thereon a unique serial number that is read by a conventional optical character reader when the welded end plug end of a tube is reciprocated into and back out of station 220 by an associated pinch wheel drive. The unique serial number provides an identifying reference for each cladding tube and enables the creation of a traceable data base for each tube as it progresses through apparatus 20, as well as subsequent manufacturing operations culminating in a completed nuclear fuel rod. The reader relays the serial number of each end plug to data acquisition system 28 for storage and later retrieval. Once a particular serial number has been stored, all subsequently acquired test data relating to that tube are correlated with that serial number for manufacturing and quality assurance record keeping purposes. In addition, weld parameter data taken during the performance of each end plug weld in welding station 100 is held for correlation with the serial number of the involved end plug. Such weld parameter data, monitored at control panel 106 (FIG. 1) includes weld current magnitude and duration, voltage, tube RPM, gas flow, etc. Maintaining a record of weld parameter data for each end plug weld enables tracking the welding process and recognition of process excursions.

Figure 9:
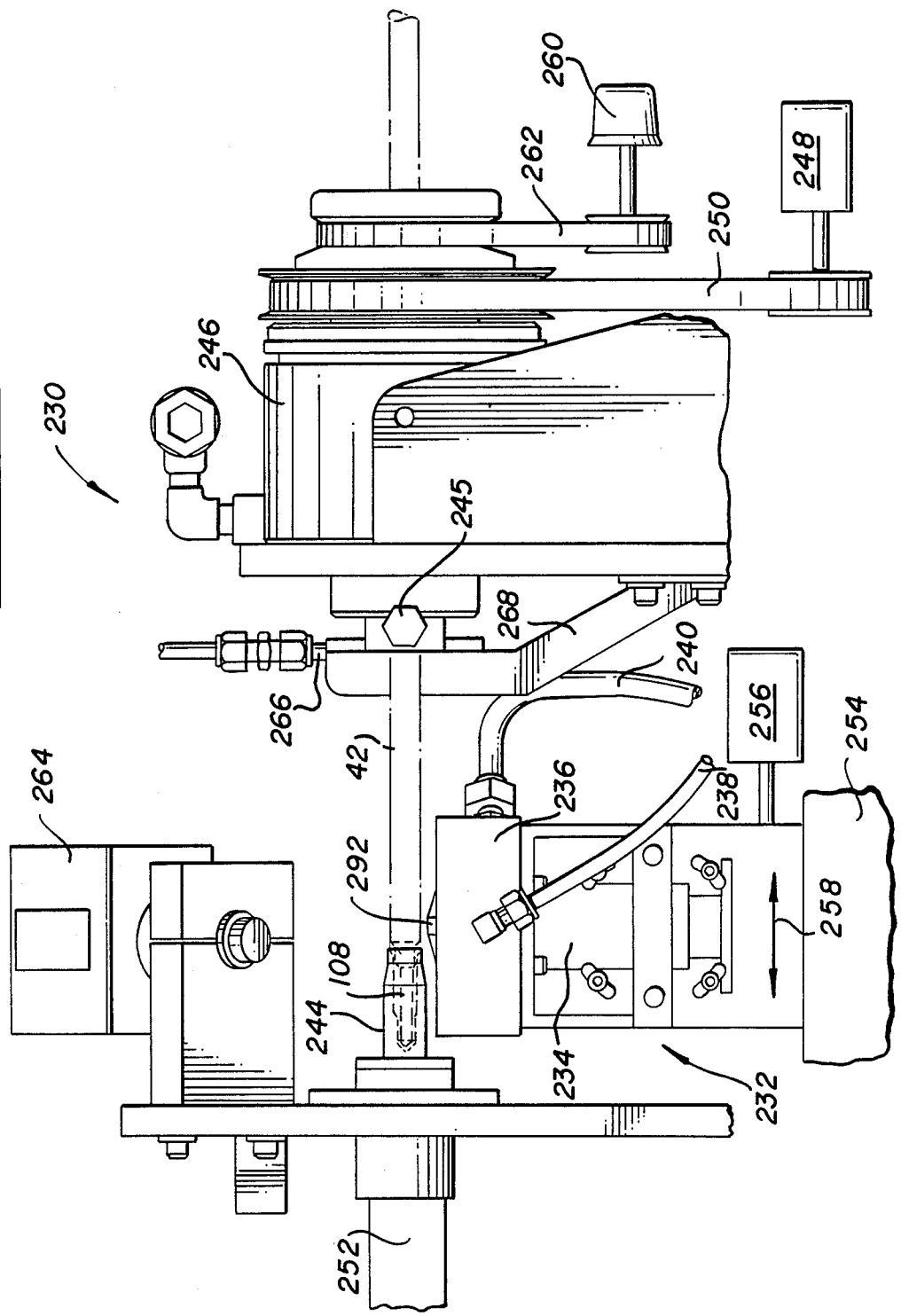
FIG. 9 shows a side view of a first weld inspection station of the first weld apparatus in FIG. 1 for ultrasonically inspecting each end plug weld.

As seen in FIG. 1, from serial number reader station 220, each tube is indexed to a weld inspection station 230. As illustrated in FIG. 9, this weld inspection station includes ultrasonic inspection (UT) apparatus, generally indicated at 232, including an ultrasonic transducer 234 positioned directly beneath a water bubbler 236. Water flows into the bubbler through an inlet conduit 238 and exits through an outlet conduit 240. Water bubbles up into contact with the end plug weld via a bubbler head 242 to provide a fluid couplant for ultrasonic probing signals both transmitted and received by the transducer. From the received echo, signals are transmitted to the data acquisition computer and are processed to develop test data indicative of weld integrity, weld dimensions, tube wall thickness proximate the weld, and the welded position of the end plug in the tube end. This test data is compared against established standards to automatically determine whether the end plug weld is acceptable or not. The results are correlated with the previously entered serial number of the end plug whose weld has just been inspected and printed out by printer 34 (FIG. 1). The test results may be displayed on an essentially real time basis by monitor 30.

To perform this inspection, when a tube is indexed to the ultrasonic test station position by transporter 44, the associated pinch wheel drive 60 is activated to propel the tube lengthwise into this station. A photocell 245 senses the arrival of a tube and signals the pinch wheel drive to reduce the tube entry speed. When the end plug end of the tube encounters a live centering stop 244, the pinch wheel drive motor stalls and is de-energized. An air chuck 246 is then actuated to clamp onto the tube, and motor 248 is energized to rotate the air chuck and tube via a belt drive 250. Live centering stop 244 is backed by an air cylinder 252 operating to exert an axial force on the live centering stop to ensure that it rotates in unison with the end plug received therein. The end plug weld is thus precisely positioned with respect to transducer 234, and an ultrasonic scan thereof is executed in a tight spiral pattern with a pitch on the order of two mils. Thus, in addition to tube rotation, the UT inspection apparatus is mounted on a slide 254 such that it can be periodically axially incremented a predetermined multiplicity of times during each tube revolution by a precision stepping motor 256, as indicated by arrow 258. Synchronized pulsing of the ultrasonic transducer and axial incrementing of the UT inspection apparatus are controlled by an encoder 260 driven in unison with air chuck 246 via a timing belt 262. Again, the tube is preferably lifted from transporter rollers 52 and radially controlled by deployed arms during tube rotation by motor 248.

Ultrasonic weld inspection station 230 further includes a second television camera 264 which is used to image the end plug serial number should serial number reader station 220 fail to correctly do so. The serial number is displayed on monitor 30 (FIG. 1), thereby enabling an alerted operator to manually enter the end plug serial number via welder display panel 106.

At the conclusion of an untrasonic scan of the end plug weld, motor 248 is de-energized, and air chuck releases the tube, enabling the associated pinch wheel drive to propel the tube back out of the ultrasonic inspection station 230. As the plug end departs, a blast of air from a nozzle 266 blows any water left thereon from bubbler 236. This water is carried off by a drain 268.

Figure 10:
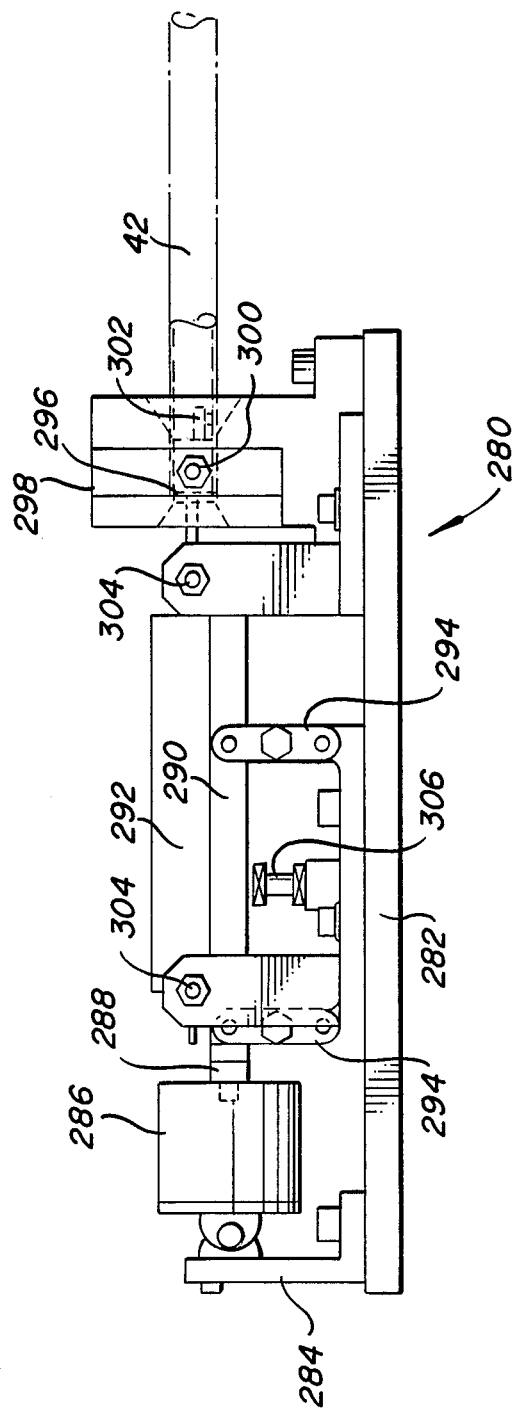
FIG. 10 is a side view of a cladding tube barrier detection station utilized in the first weld apparatus of FIG. 1.

In the illustrated embodiment of FIG. 1, each tube 42 is next indexed by transporter 44 to a barrier detection station 280 to determine the presence and thickness of any zircalloy liner applied to the tube interior surface. Thus, this staion is disposed at a transporter index position aligned with the open, tail end of a tube opposite its welded end plug end. As shown in FIG. 10, barrier detection station 280 includes a base plate 282 to which is attached a bracket 284 for pivotally mounting an air cylinder 286. The air cylinder piston 288 is pivotally connected to a holder 290 for the body 292 of an eddy current sensor. This sensor holder is pivotally mounted to base 282 by a four-bar mechanism, two bars of which are indicated at 294. As a tube is propelled into barrier detection station 280, its open tail end encounters a stop 296 positioned within the open bore of a sensor block 298. The associated pinch wheel drive motor stalls and stops. Tube arrival is signalled by a proximity sensor 300. With the open tail end of a tube properly positioned within sensor block 298, air cylinder 286 is actuated to swing the sensor body 292 forwardly on four-bar mechanism 294 and thus lower an eddy current probe 302 into contact with the interior surface of the tube. The probe is energized to induce eddy currents in the tube and detect the same. The magnitude of the detected eddy currents indicates whether a zirconium linear is present and, if so, its thickness. Data generated by the eddy current sensor is relayed to data acquisition computer for correlation with the appropriate tube serial number. Proximity sensors 304 monitor and coordinate the operations automatically performed in barrier detection station 280. An adjustable stop 306 establishes the ultimate eddy current probe test position. Upon completion of this test, air cylinder swings the sensor rearwardly, raising probe 302 out of contact with the tube interior surface, and the tube is propelled back out onto transporter 44 by the associated pinch wheel drive.

As shown in FIG. 1, the barrier detection station data is preferably taken after the end plug welding operation. This allows the information relating to the zirconium liner to be readily correlated with the appropriate end plug serial number. However, the barrier detection station could be located elsewhere in the sequence of stations, even prior to welding station 100. Doing so would require a special procedure for correlating the results of this inspection with a tube whose serial number has yet to be assigned by the welding of an end plug thereto.

Figure 11:
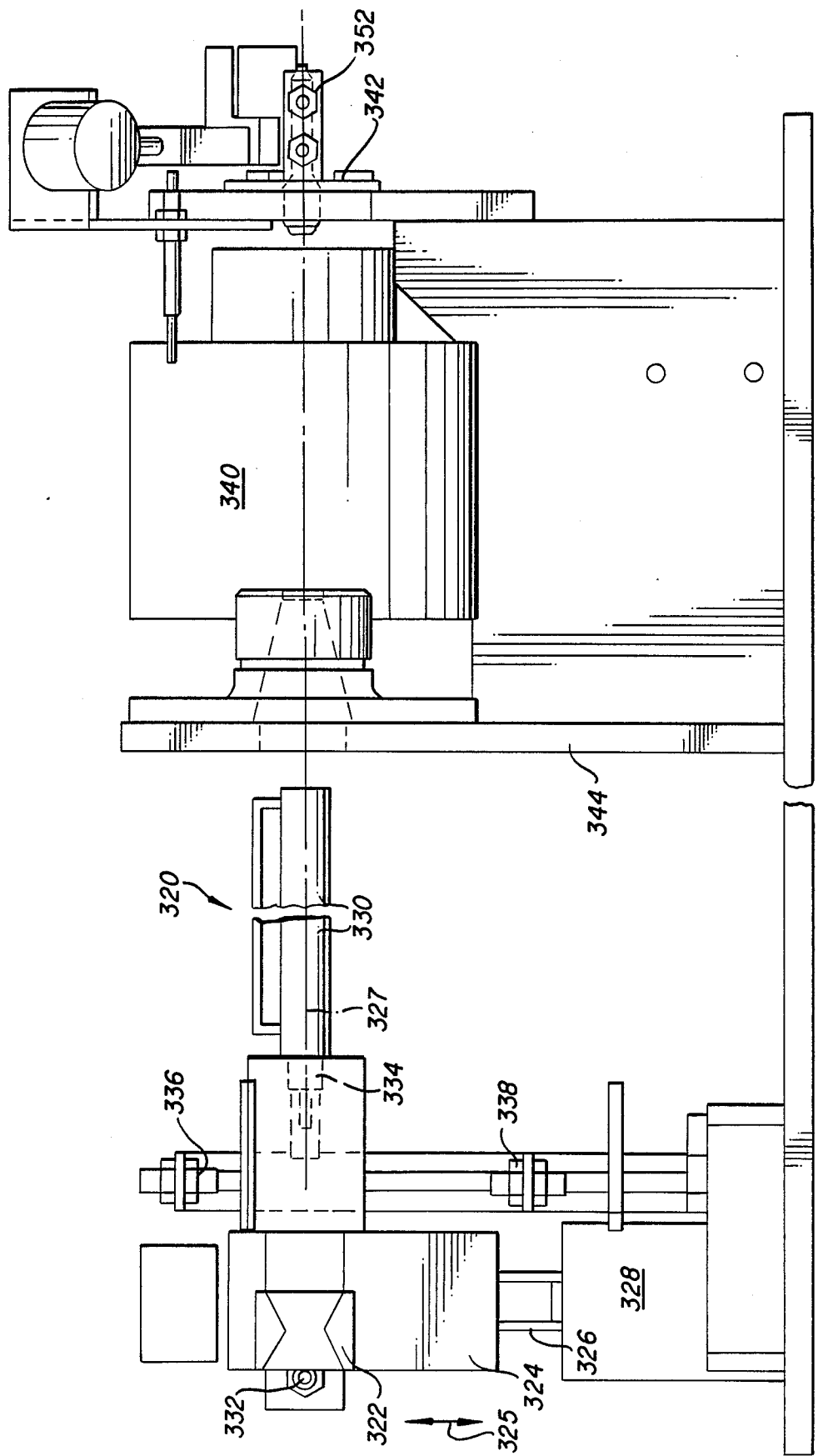
FIG. 11 is a side elevational view of a second weld inspection station utilized in the first weld apparatus of FIG. 1.
Figure 12:
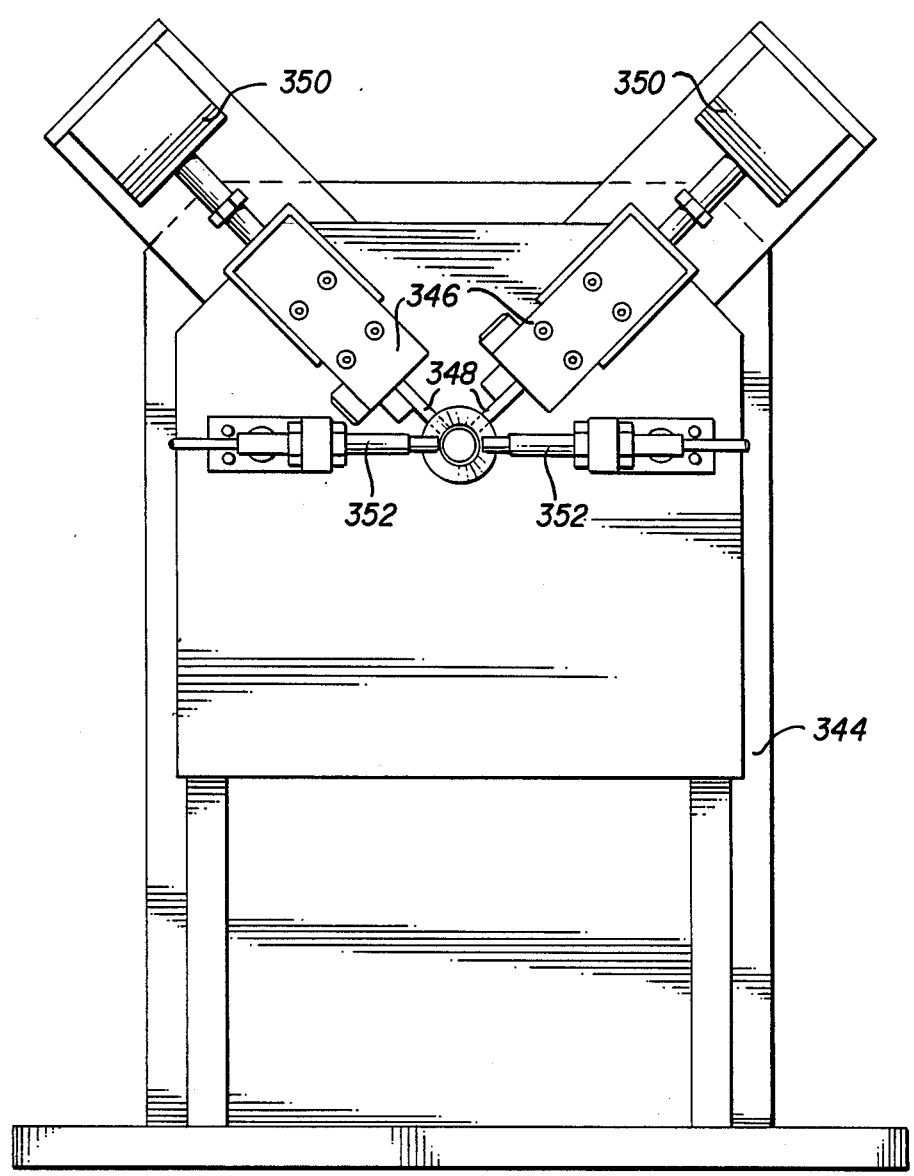
FIG. 12 is an end view of the second weld inspection station.
Figure 12A:
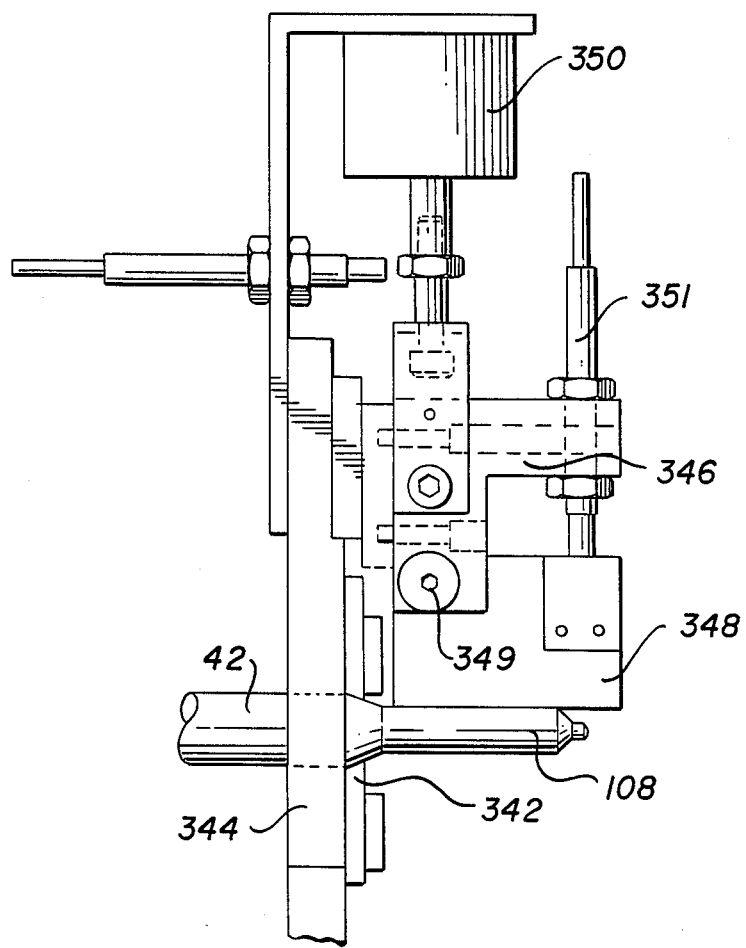
FIG. 12A is a view taken along line 12A—12A of FIG. 12.

From barrier detection station 280, each tube 42 is next indexed to a second weld inspection station 320, seen generally in FIG. 1 and in greater detail in FIGS. 11, 12 and 12A. This inspection station includes a ring gauge 322 carried by a fixture 324 which, in turn, is reciprocatingly mounted, as indicated by arrow 325, by a pair of vertical columns, one seen at 326. The fixture is selectively positioned by an air cylinder 328 to an illustrated elevated position with the ring gauge aligned with the path (centerline 327) of tube insertion into inspection station 320 and to a lowered position clearing the fixture from the tube insertion path. Fixture 324 also carries an air cylinder 330 which is aligned with the tube insertion path when the fixture is in its elevated position and clear thereof when the fixture is in its lowered position.

The arrival of the end plug leading end of a tube at inspection station 320, as propelled by an associated pinch wheel drive 60 (FIG. 1), is signalled by a photocell 332. If the weld diameter is less than a specified maximum diameter, as established by ring gauge 322 in its fixture elevated position, the tube passes freely therethrough until the end plug tip encounters the piston 334 of air cylinder 330. This event is signalled by the tube's interruption of a light beam extending from a source 336 to a detector 338, and the computer system 28 is advised that the end plug weld diameter of this tube does not exceed the specified maximum. The pinch wheel drive stalls, its motor is stopped, and its pinch wheel is elevated from the tube. Air cylinder 330 is actuated, and its piston 334 drives the tube back out of inspection station 320. When this piston is retracted and the ring gauge is thus cleared, air cylinder 326 is actuated to pull fixture 324 downwardly to its lowered position. The tube insertion path is then cleared, and the associated pinch wheel drive again propels the tube into inspection station 320 and through an air chuck 340 until its end plug end encounters a stop 342 stationed therebeyond. The pinch wheel drive stalls and is stopped. Air chuck 340, mounted by a stand 344, is actuated to clamp the tube with its axis precisely oriented in a fixed reference position. Stand 344 also mounts a pair of suitable gauge fixtures 346 angularly oriented 90° apart, as seen in FIG. 12. As seen in FIG. 12A, the blades 348 of these fixtures, which are pivotally mounted at 349, are driven into contact with the end plug peripheral surface by respective air cylinders 350, and the extents of the blade movements are accurately measured by sensors 351, which may be eddy current sensors, and communicated to the computer system. From these measurements, the position of the end plug axis is accurately calculated to determine the extent of any non-parallelism between tube axis and the end plug axis. In addition, a pair of diametrically opposed proximity sensors 352 measure the end plug outer diameter and signal the computer system accordingly.

Should the end plug weld diameter fail the ring gauge test and hang up in ring gauge 322, the fact that the light beam between source 336 and detector 338 was not broken within a given time period after tube arrival was detected by photocell 332 is signalled to the computer system. Although the tube is rejectable because of excessive weld diameter, it is still desireable to check for axes parallelism and to measure end plug diameter. Thus air cylinder 330 is fired to back the rejected tube out to clear the ring gauge, and air cylinder 328 is fired to drop fixture 324 and air cylinder 330 to their lowered position clearing the tube insertion path. The pinch wheel drive is then activated to drive the rejected tube forwardly through air chuck 340 to stop 342 so these tests can be performed. The tube is then backed out of inspection station 320 and fully onto tube transporter 44 preparatory to the next indexing step.

As previously indicated, computer system 28 compares the test data generated at each inspection station against pre-established quality control standards. If any end plug weld is found to be beyond permissible tolerance limits, an automatic sorting station, generally indicated at 400 in FIG. 13, operates to separate rejected tubes from accepted tubes. When transporter 44 steps each tube to its final index position, it is presented at this sorter station. Included therein are a plurality of sorter hands spaced along the tube length, one seen at 402, which are affixed to a shaft 404 rotatably mounted just beyond the final index position in parallel relation to a tube 42 positioned thereat. A reject tray 406 is positioned to accept rejected tubes from the sorter hands 402. Each identical sorter hand carries diametrically opposed sets of three fingers 408, 410, and 412. An accept slot 414 is provided between fingers 408 and 410 of each hand, while a shallower reject slot 416 is provided between fingers 410 and 412. Controller 26, in response to a signal from computer system 28, selectively, angularly positions these hands, such that, upon the next transporter indexing step, an accepted tube is picked off in accept slots 414, while a rejected tube is picked off in reject slots 416. The hands are then jointly rotated in the clockwise direction to transfer rejected tubes to reject tray 406 and accepted tubes to a conveyor 418. Accepted rods are held in the sorter hands by offset tips 420 until fingers 408 have swung downwardly to the point where the accepted tubes will be transferred by ramps 421 onto a rod conveyor 418. With the sorting of a tube by one set of fingers, the other, opposed set is in approximate position to sort the next tube.

Figures 13, 14:
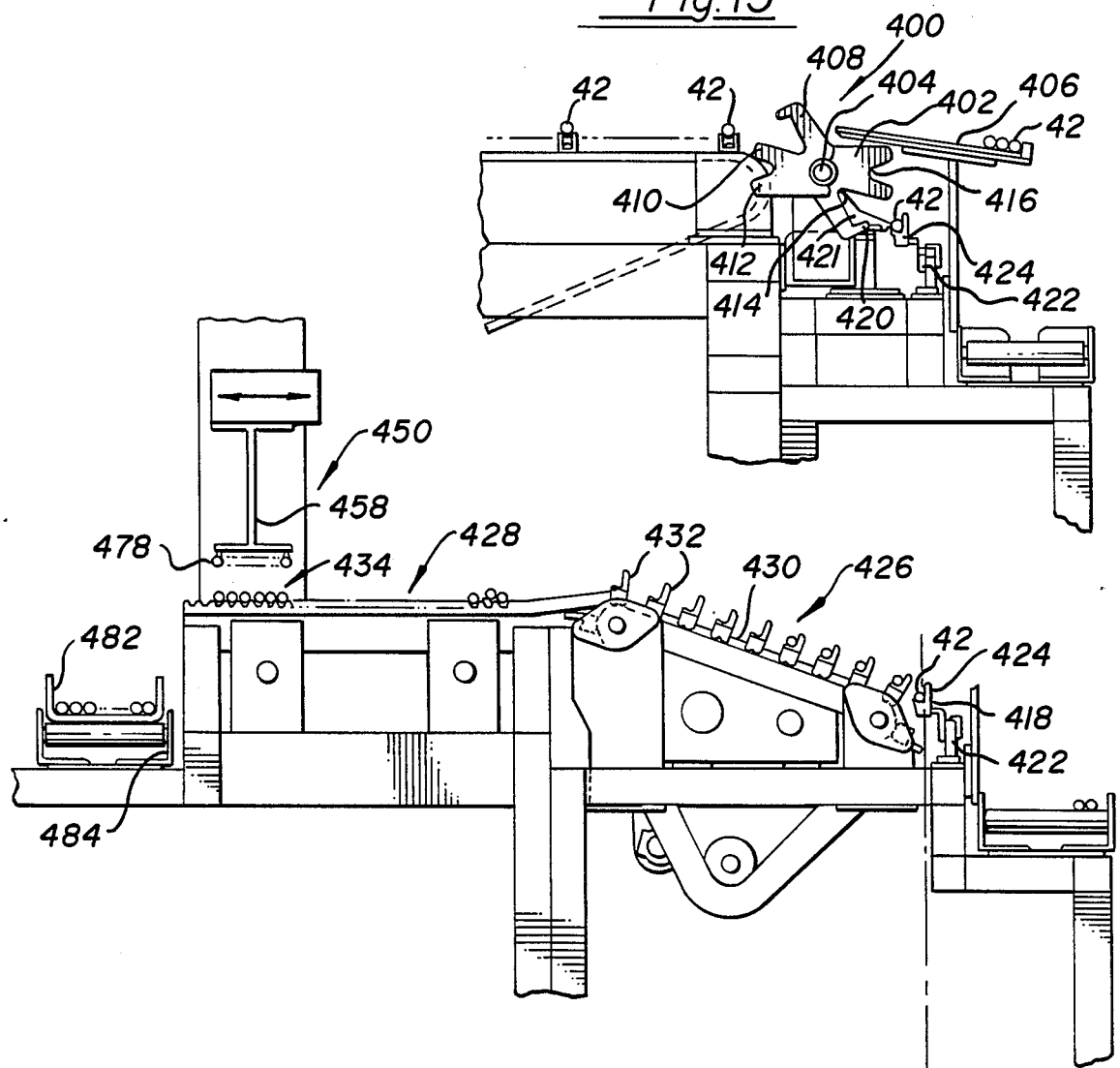
FIG. 13 is an end view of an accept/reject tube sorter utilized in the apparatus of FIG. 1.
FIG. 14 is an end view of the off load accumulator and visual inspection section of the first weld apparatus of FIG. 1.

Rod conveyor 418, which is schematically indicated by arrow 418a in FIG. 1, conveys each accepted rod to offload accumulator and visual inspection section 24. Thus, this conveyor includes, as seen in FIG. 13, an endless chain 422 mounting a distributed plurality of tube carriers 424 upon which accepted tubes rest for endwise conveyance. When an accepted tube arrives at offload accumulator and visual inspection section 24, it is picked up by an elevator, generally indicated at 426 in FIG. 14, for conveyance to a walking beam conveyor, generally indicated at 428. The elevator includes a plurality of parallel conveyor chains 430, each equipped with a succession of longitudinally aligned carriers 432 on which the tubes rest for transport. Each tube transferred to walking beam conveyor 428 is propagated to a visual inspection station 434 where an inspector examines it for weld discoloration and other cosmetic blemishes. Preferably, as each tube arrives at section 24, it is picked up by elevator 426 and transferred directly to visual inspection station 434 until a predetermined number of tubes are accumulated thereat. The inspector then examines the tubes as a group by manually spinning the tubes as supported in the inspection station on rollers (not shown).

As shown in FIG. 14, elevator 426 includes carrier positions for nine tubes with a tenth held in a pickup position on conveyor 418. Walking beam conveyor 428 may be of any desired length to accumulate an additional plurality of tubes in a queue awaiting visual inspection. When the tubes have been visually inspected and offloaded from visual inspection station 434, elevator 426 and walking beam conveyor 428 are activated to fill the inspection station with another group of tubes. By virtue of this arrangement, there should be ample queuing capacity for tubes awaiting visual inspection to avoid having to interrupt the end plug welding and inspection operations of section 22. While not shown, strategically located sensors monitor the positions of the tubes in the queue and signal controller 26 to activate the various tube conveyors such as to promptly fill inspection station 434 once accepted tubes have been offloaded therefrom.

Figure 15:
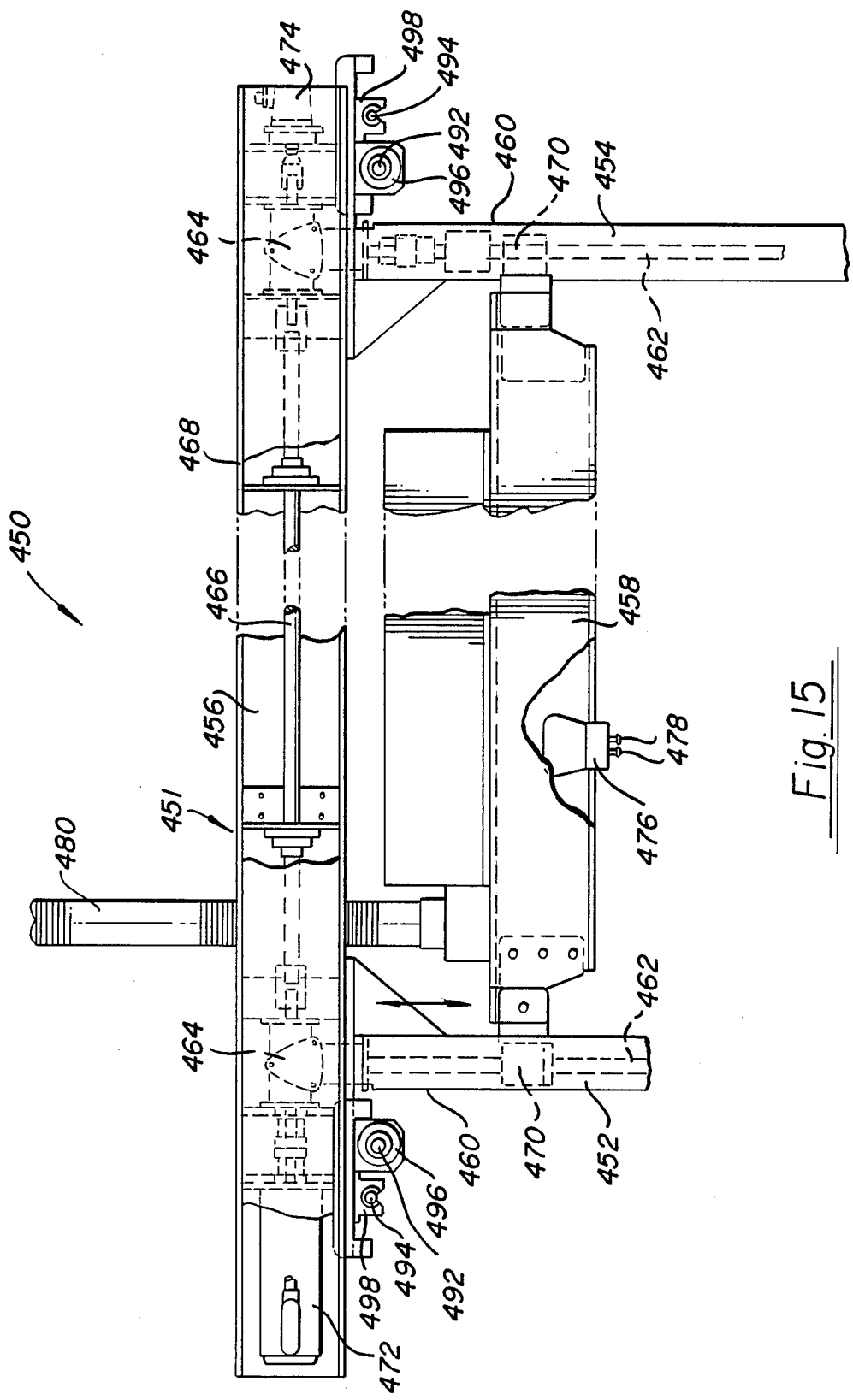
FIG. 15 is a side elevational view of an offload vacuum pick-up mechanism for removing accepted tubes from the visual inspection station.
Figure 16:
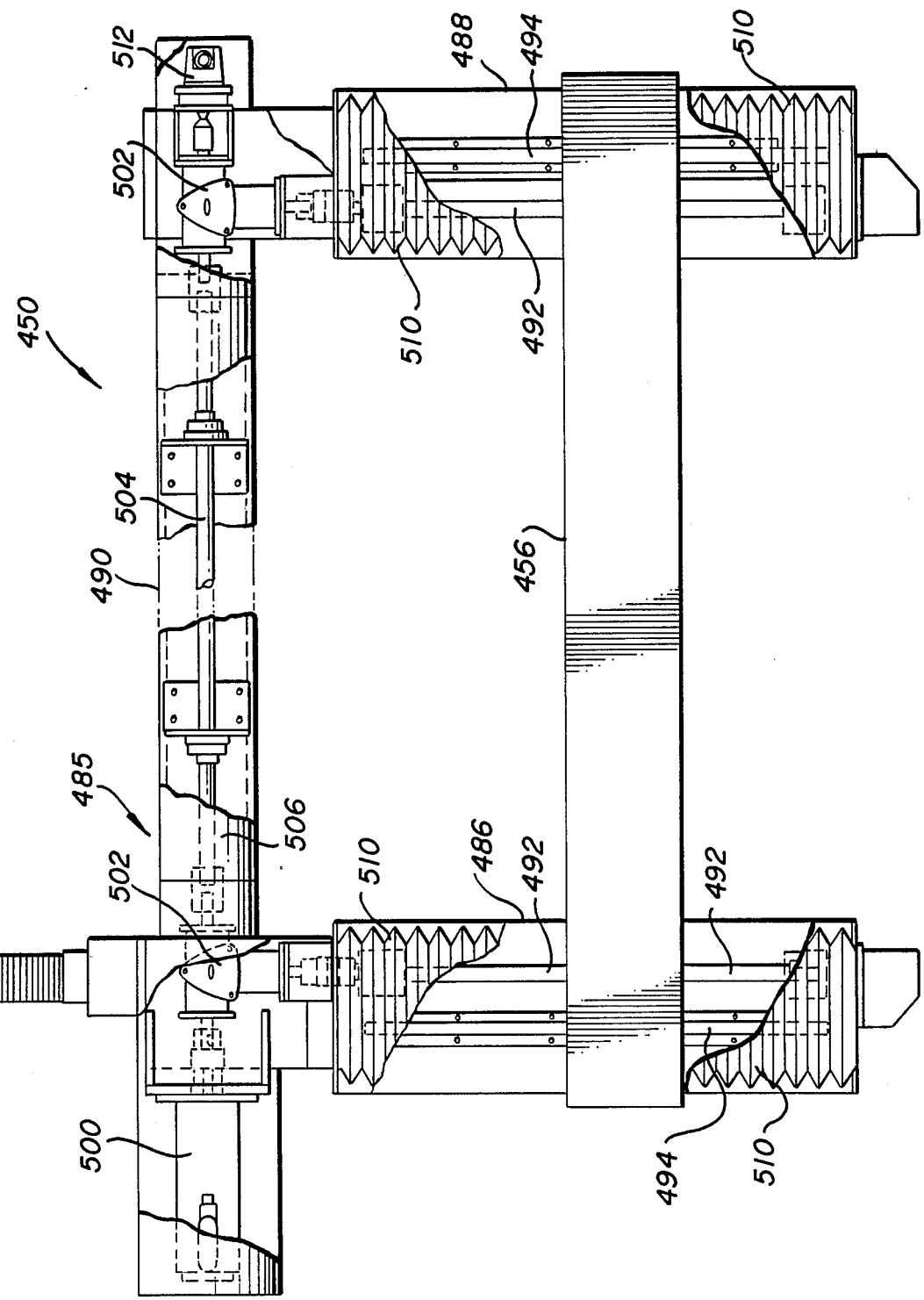
FIG. 16 is a plan view of the offload vacuum pickup mechanism of FIG. 15.

To offload the accepted tubes from this visual inspection station, a vacuum pick up mechanism, generally indicated at 450 in FIGS. 1 and 14, and detailed in FIGS. 15 and 16, is triggered into operation. Referring first to FIG. 15, this vacuum pickup mechanism includes a vertical drive mechanism, generally indicated at 451, which consists of a pair of vertical drive legs 452 and 454, a horizontal drive leg 456, and a horizontal pickup beam 458. Each vertical drive leg includes a housing 460 enclosing and mounting a ball screw shaft 462 which is driven from separate double output gearboxes 464 interconnected by a cross shaft 466 enclosed and mounted by a horizontal drive leg housing 468. Each ball screw shaft carries a travelling nut 470 supporting pickup beam 458 at its opposite ends. A servo motor 472, mounted in horizontal drive leg housing 468, drivingly rotates the ball screw shafts of vertical drive legs 452 and 454 in unison via gear boxes 464 and cross shaft 466, as well as a position encoder 474. It is seen that ball screw shaft rotation vertically translates pickup beam 458 via travelling nuts 470 while preserving its horizontal orientation. Pickup beam 458 includes a plurality vacuum generators (not shown). These vacuum generators are actuated to pull a vacuum on a plurality of suction cups 478 mounted in a plurality of plunger blocks 476 in response to signals communicated thereto over leads running in a flexible wire duct 480.

In operation, pickup beam 458 is normally poised in a raised position over visual inspection station 434 (FIG. 14). After the quality assurance technician has completed a visual inspection of the tubes, controller 26 is signalled to activate servo motor 472. Pickup beam 458 is lowered to bring suction cups 478 into contact with the tubes resting in the visual inspection station at a multiplicity of points spaced along their length. A vacuum is then pulled on the suction cups, and the accepted tubes are held thereto. Servo motor 472 is then reversed in drive direction, and the pickup beam is elevated to lift the accepted tubes away from visual inspection station 434. The lifted tubes are then transferred horizontally and lowered into an accepted tube tray 482 resting on a roller conveyor 484, as seen in FIG. 14.

To accomplish the horizontal transfer motion of the accepted tubes, vacuum pickup mechanism 450 further includes, as seen in FIG. 16, a horizontal drive mechanism, generally indicated at 485, consisting of a pair of horizontal drive legs 486, 488 and an interconnecting horizontal drive leg 490. Each horizontal drive leg serves to mount a ball screw shaft 492 and a Thomson shaft 494 in closely spaced parallel relation. As seen in FIG. 15, the ball screw shafts 492 carry travelling nuts 496 affixed to the horizontal drive leg 456 of vertical drive mechanism 451 adjacent each end thereof. In addition, horizontal drive leg 456 carries adjacent each end a sliding guide 498 which substantially embraces the Thomson shaft 494 of each horizontal drive leg 486, 488. It is thus seen that the vertical drive mechanism 451 of FIG. 14 is mounted by the horizontal drive legs 486, 488 of horizontal drive mechanism 485 for precision guided horizontal movement.

To effect this horizontal movement, coordinated driving rotation of the horizontal drive leg ball screw shafts 492 is produced by a servo motor 500 acting via double output gear boxes 502 and an interconnecting cross shaft 504, all enclosed and mounted within horizontal drive leg housing 506. Travelling nuts 496 translate uniformly on ball screw shafts 492, and pickup beam 458 is moved horizontally from an elevated position above visual inspection station 434 to an elevated position over tray 482 (FIG. 14). The vertical drive mechanism 451 then takes over to lower the pickup beam into tray 482. The suction grip on the tubes exerted by suction cups 478 is released, and the tubes are deposited in the tray. The vertical and horizontal drive mechanisms are then activated in sequence to return the pickup beam to its ready position elevated above visual inspection station 434. Preferably, the horizontal drive legs 486 and 488 are enclosed by flexible boots 510. The horizontal position of the pickup beam is monitored by a position encoder 512 driven off of servo motor 500.

Having thus described both the apparatus and its operation in some detail it will be apparent to those skilled in the art that various changes, modifications, substitutions and equivalent may now suggest themselves, all of which fall within the spirit and scope of the invention as defined by the appended claims.

What is claimed as new and desired to secure by Letters Patent is:

1. Automated apparatus for welding a separate end plug to one open end of each of a succession of nuclear fuel cladding tubes and for inspecting each end plug weld, said apparatus comprising, in combination:
   A. a welding station including:
      (1) a supply of end plugs,
      (2) end plug handling means for picking individual end plugs from said supply for mating with one open end of each tube successively presented to said welding station, and
      (3) a welder operating to weld the mated end plug to the tube;
   B. a serial number reader station for reading a unique serial number imprinted on each end plug;
   C. a weld inspection station for inspecting each end plug weld and for generating weld inspection data indicative of the weld characteristics;
   D. data acquisition means linked with said serial number reader station and said weld inspection station and operating to correlate the weld inspection data with the associated end plug serial number for each end plug weld;
   E. an input queue for holding a quantity of tubes; and
   F. a tube transporter for periodically picking individual tubes from said input queue and conveying said tubes successively to said welding station, said serial number reader station, and said weld inspection station.

2. The apparatus defined in claim 1, wherein said tube transporter conveys the tubes in a direction transverse to their tube axis in indexing steps to index positions respective axially aligned with said stations, said transporter further including separate drive means positioned at said index positions for axially reciprocating the tubes into and out of said stations.

3. The apparatus defined in claim 2, wherein said tube transporter further includes a plurality of parallel spaced, endless conveyor chains carrying grooved rollers at corresponding spaced intervals, each tube being supported on an aligned set of said rollers.

4. The apparatus defined in claim 3, wherein each said drive means includes a bidirectionally driven pinch roller coacting with one of said grooved rollers to axially reciprocate a tube positioned therebetween.

5. The apparatus defined in claim 2, wherein said welding station includes a weld box enclosing said welder and into which the one open end of each tube is successively positioned by said drive means, said end plug handling means includes a manipulator and a mating ram carrying an adapter at one end, said manipulator picking individual end plugs from said supply and placing same in said adapter, and motive means for driving said ram into said weld box to mate the end plug held by said adapter with the tube open end positioned therein.

6. The apparatus defined in claim 5, wherein said welding station further includes means for commonly rotating said tube and said ram during the welding of the mated end plug to the tube.

7. The apparatus defined in claim 6, wherein said welder is a tungsten electrode-inert gas welder.

8. The apparatus defined in claim 7, wherein said weld station further includes a TV camera for imaging the interior of said weld box to provide a visual aid in the proper positioning of said welder electrode.

9. The apparatus defined in claim 7, wherein said weld station further includes means selectively operable to preheat said end plug-holding adapter prior to a end plug welding operation.

10. The apparatus defined in claim 1, wherein said weld station further includes means for generating weld parameter data pertaining to each end plug weld for correlation with the serial number of the associated end plug by said data acquisition means.

11. The apparatus defined in claim 5, which further includes a cooldown station having an enclosure into which the end plug welded end of each tube is immediately introduced by said tube transporter upon withdrawal from said weld station by said drive means, said cooldown station including means within said enclosure for bathing the end plug welds with streams of an inert cooling gas as the tubes are indexed therethrough by said tube transporter.

12. The apparatus defined in claim 11, wherein cooldown station enclosure is at least two tube index positions in length.

13. The apparatus defined in claim 2, wherein said weld inspection station includes an ultrasonic transducer for inspecting each end plug weld.

14. The apparatus defined in claim 13, wherein said weld inspection station further includes a bubbler of ultrasonic energy couplant liquid in which each end plug weld is positioned.

15. The apparatus defined in claim 14, wherein said weld inspection station further includes a live centering stop against which the end plug end of each tube is engaged when inserted into said weld inspection station by said tube transporter drive means, and means for rotating each tube to unltrasonically scan its end plug weld.

16. The apparatus defined in claim 15, wherein said weld inspection station further includes means for jointly incrementing said bubbler and transducer in a direction parallel to the tube axis to perform a spiral scan of the end plug weld.

17. The apparatus defined in claim 16, wherein said weld inspection station further includes a TV camera for imaging the end plug serial number to enable manual entry thereof into said data acquisition means in the event said serial number reader station fails to correctly read the serial number.

18. The apparatus defined in claim 2, which further includes a barrier detection station into which the other open end of tube is reciprocated by said tube transporter drive means, said barrier detection station including means for detecting the presence and sensing the thickness of any zirconium barrier on the interior surface of each tube, said barrier detection station linked with said data acquisition means to enter barrier data for correlation with the associated end plug serial number.

19. The apparatus defined in claim 18, wherein said barrier detection station includes an eddy current probe and means for articulating said probe into barrier sensing relation with each tube propelled into and out of said barrier detection station by said tube transporter drive means.

20. The apparatus defined in claim 2, which further includes a second end plug weld inspection station into which each tube is reciprocated by said tube transporter drive means, said second weld inspection station including means for gauging whether each end plug weld outer diameter exceeds a predetermined limit.

21. The apparatus defined in claim 20, wherein said gauging means includes a ring gauge, means for positioning said ring gauge in the tube entry path into said second weld inspection station, and a sensor responsive to the failure of a welded end plug to pass through said ring gauge for signalling said positioning means to remove said ring gauge from said tube entry path and thus permit full inspection of the tube into said second weld inspection station by said tube transporter drive means.

22. The apparatus defined in claim 21, wherein said second weld inspection station further includes means to check for any nonparallelism between the end plug and tube axes of each tube fully inserted into said second weld inspection station.

23. The apparatus defined in claim 2, which further includes means linked with said data acquisition means for processing said weld inspection data to determine whether each end plug weld meets established engineering standards and to issue appropriate accept/reject signals in correlation with the associated end plug serial number, and a sorter operating in response to said accept/reject signals for separating accepted tubes from rejected tubes.

24. The apparatus defined in claim 23, which further includes a tube conveyor for conveying accepted tubes successively away from said sorter, a visual inspection station capable of accepting a predetermined plurality of tubes in parallel, side-by-side relation, and an output queuing conveyor for successively conveying accepted tubes from said tube conveyor to fill said visual inspection station with said predetermined number of tubes.

25. The apparatus defined in claim 24, which further includes an off-load transfer mechanism for transferring those tubes passing visual inspection as a group from said visual inspection station to an accepted tube tray conveyor.

26. Automated apparatus for welding a separate end plug to one open end of each of a succession of nuclear fuel cladding tubes and for inspecting each end plug weld, said apparatus comprising, in combination:
A. a welding station including
 (1) a supply of end plugs,
 (2) end plug handling means for picking individual end plugs from said supply for mating with one open end of each tube successively presented to said welding station, and
 (3) a welder operating to weld the mated end plug to the tube;
B. a cooldown station for cooling each end plug weld in an inert gas atmosphere;
C. a serial number reader station for reading a unique serial number inprinted on each end plug;
D. a first weld inspection station for inspecting each end plug weld and for generating first weld inspection data indicative of the weld internal characteristics;
E. a second weld inspection station for inspecting each end plug weld and generating second weld inspection data indicative of the weld external characteristics;
F. a computer system linked with said serial number reader and said first and second weld inspection stations, said computer system operating to correlate said first and second weld inspection data with the associated end plug serial number for each end plug weld and processing said inspection data to determine whether each end plug weld meets established engineering standards pursuant to issuing appropriate accept/reject signals in correlation with the associated end plug serial number;
G. an input queue for holding a plurality of tubes;
H. a tube transporter for periodically picking individual tubes from said input queque and conveying the tubes in a direction transverse to their tube axis in indexing steps to index positions respectively axially aligned with said welding, serial number reader, and first and second weld inspection stations, said tube transporter including separate drive means positioned at said index positions for axially reciprocating the tubes into and out of said welding, serial number reader, and first and second weld inspection stations; and
I. a sorter positioned at an output end of said tube transporter and operating in response to said accept/reject signals from said computer system to sort the tubes successively transported thereto into separate accept and reject lots.

27. The apparatus defined in claim 26, wherein said welding station includes a weld box enclosing said welder and into which the one open end of each tube is successively positioned by said tube transporter drive means, said end plug handling means including a manipulator and a mating ram carrying an adapter at one end, said manipulator picking individual end plugs from said supply and placing same in said adapter, and means for driving said ram into said weld box to mate the end plug held by said adapter with the tube open end position therein.

28. The apparatus defined in claim 27, wherein said welding station further includes means for commonly rotating said tube and said ram during the welding of the mated end plug to the tube.

29. The apparatus defined in claim 28, wherein said first weld inspection station includes an ultrasonic transducer for ultrasonically scanning each end plug weld.

30. The apparatus defined in claim 29, wherein said first weld inspection station includes a live centering stop against which the end plug of each tube is engaged when inserted into said first weld inspection station by said tube transporter drive means, means for rotating each inserted tube, and means for incrementing said transducer in a direction parallel to the tube axis to perform a spiral ultrasonic scan of each end plug weld.

31. The apparatus defined in claim 30, wherein said first weld inspection station further includes a TV camera for imaging the end plug serial number of an inserted tube to enable manual entry thereof into said computer system in the event said serial number reader station fails to correctly read the end plug serial number.

32. The apparatus defined in claim 26, which further includes a barrier liner inspection station into which the open end opposite the welded end plug end of each tube is reciprocated by said tube transporter drive means, said barrier liner inspection station including means for detecting the presence and thickness of any barrier liner applied to the tube interior surface.

33. The apparatus defined in claim 32, which further includes a tube conveyor for conveying accepted tubes successively away from said sorter, a visual inspection station capable of accepting a predetermined plurality of tubes in parallel, side-by-side relation, and an output queing conveyor for successively conveying accepted tubes from said tube conveyor to fill said visual inspection station with said predetermined number of tubes.

34. The apparatus defined in claim 33, which further includes an off-load transfer mechanism for transferring those tubes passing visual inspection as a group from said visual inspection station to an accepted tube tray conveyor.

35. The apparatus defined in claim 26, wherein said welding station further includes means for generating weld parameter data pertaining to each end plug weld, said computer system correlating said weld parameter data for each end plug weld with the serial number of the involved end plug.

* * * * *